US005609576A

United States Patent [19]
Voss et al.

[11] Patent Number: 5,609,576
[45] Date of Patent: Mar. 11, 1997

[54] FLUID FLOW IMPEDANCE MONITORING SYSTEM

[75] Inventors: Gregory I. Voss, Solana Beach; Robert D. Butterfield, Poway; Gail D. Baura, San Diego; Casper W. Barnes, Murrieta, all of Calif.

[73] Assignee: IVAC Medical Systems, Inc., San Diego, Calif.

[21] Appl. No.: 305,904

[22] Filed: Sep. 13, 1994

[51] Int. Cl.$^6$ .................................................. A61M 31/00
[52] U.S. Cl. ........................ 604/67; 604/153; 604/246; 128/DIG. 13
[58] Field of Search .................... 604/50, 65, 67, 604/66, 131, 153, 49, 246; 128/DIG. 12, DIG. 13

[56] References Cited

U.S. PATENT DOCUMENTS

| | | | |
|---|---|---|---|
| 4,898,576 | 2/1990 | Philip | 604/50 |
| 4,979,940 | 12/1990 | Bobo, Jr. et al. | 604/50 |
| 5,103,211 | 4/1992 | Daoud et al. | 304/608 |
| 5,190,041 | 3/1993 | Palti | 128/635 |
| 5,213,573 | 5/1993 | Sorich et al. | 604/66 |
| 5,356,378 | 10/1994 | Doan | 604/65 |
| 5,423,743 | 6/1995 | Butterfield | 604/50 |

*Primary Examiner*—Mark Bockelman
*Attorney, Agent, or Firm*—Fulwider Patton Lee & Utecht, LLP

[57] ABSTRACT

Impedance to fluid flow in a fluid delivery line is measured. Two techniques are used depending on the flow rate selected. For high flow rates, the pump is controlled to vary the flow rate and the change in pressure is divided by the change in flow to directly determine the resistance. For low flow rates, a processor controls the pump to pump flow quantities in accordance with a pseudo-random binary code. The resulting pressure signal sensed at the conduit is decoded in accordance with that code. Pressures received during code periods of no flow are subtracted from pressures received during code periods of flow. Pressure offset is also removed and a least squares estimation approach is used with a linear prediction model to determine impedance. The coefficients determined in the model are used to calculate the resistance to fluid flow of the system. A quality supervisor monitors the resistance determination process and controls the display of resistance depending on the quality determined. A resistance display continuously displays the resistance of the system.

62 Claims, 8 Drawing Sheets

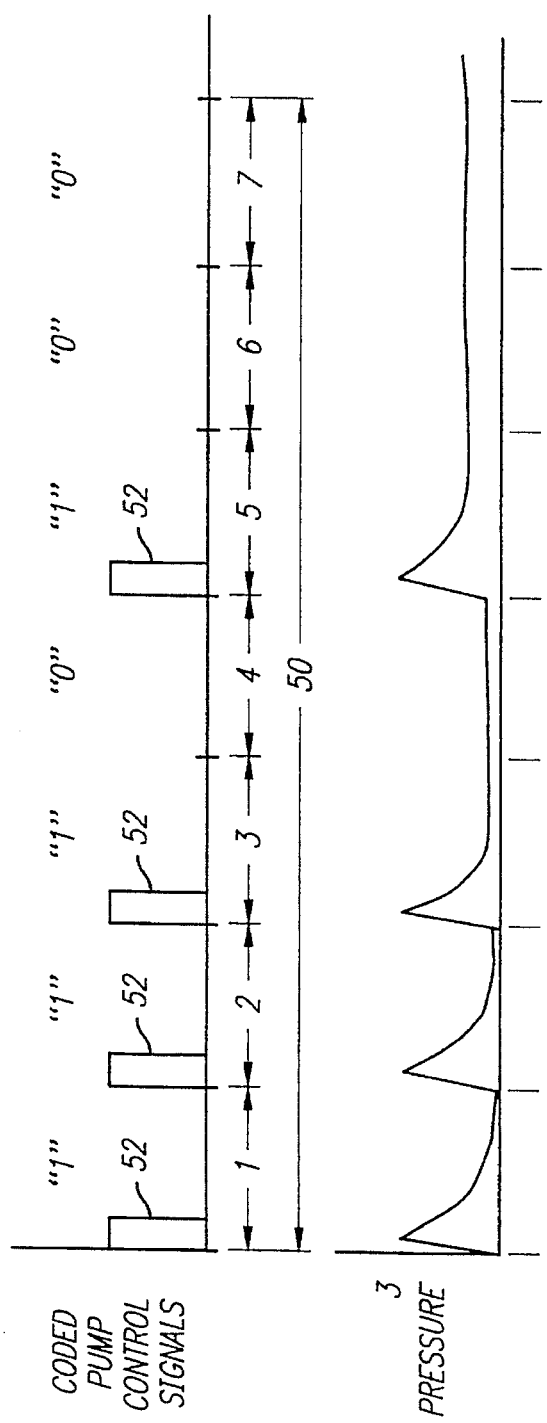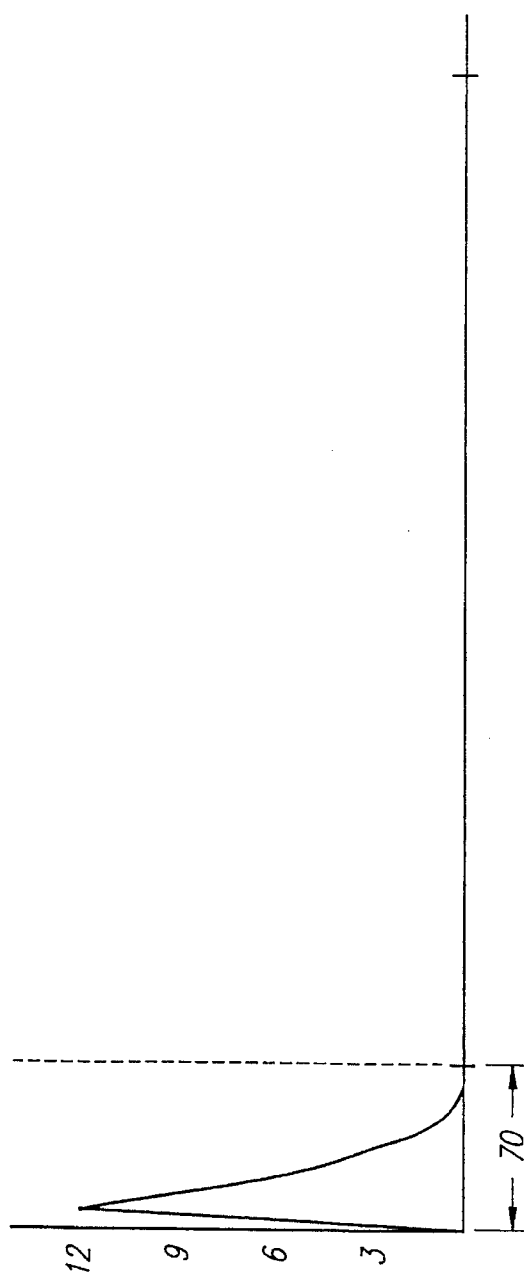
FIG. 3
FIG. 4
FIG. 5

FLUID FLOW IMPEDANCE MONITORING SYSTEM

BACKGROUND

The invention relates generally to monitoring the delivery of fluid through a conduit, and more particularly, to monitoring the impedance to fluid flow in a fluid delivery system.

Fluid delivery systems for infusing fluid to a patient typically include a supply of the fluid to be administered, an infusion needle or cannula, an administration set connecting the fluid supply to the cannula, and a flow control device, such as a positive displacement infusion pump. The cannula is mounted at the distal end of the flexible tubing of the administration set for insertion into a patient's blood vessel or other body location to deliver the fluid infusate to the patient. One commonly used flow control device is a linear peristaltic type pump having several cams and cam-actuated fingers that sequentially occlude portions of the flexible tubing along a pumping zone to create a moving zone of occlusion. The peristaltic action forces the fluid through the tubing of the administration set to the cannula and into the patient.

During an infusion procedure, events may occur that interfere with the proper administration of the infusate to the patient, such as an occlusion of the administration line. It is desirable to detect these conditions as soon as possible so that they can be remedied. A commonly used clinical technique for detecting such conditions and for evaluating fluid delivery system status is to monitor the pressure in the fluid delivery conduit. An increasing pressure may be interpreted as an occlusion.

A difficulty in determining fluid delivery system status through monitoring the downstream pressure alone is the slow speed at which pressure builds when the system is operating at a low flow rate. At low flow rates, the energy per unit time introduced into the flow path is very small. This causes difficulty in detecting a fluid line fault based on the pressure response as it may take a considerable amount of time for the pressure to build up enough to exceed a threshold and indicate an occlusion. Lowering the threshold pressure level at which a fault is indicated will cause detection to occur earlier; however, it has been found that this approach can have the effect of increasing the false alarm rate. With a relatively low pressure threshold, patient movements such as coughing, sneezing, and sitting up can cause the pressure to exceed that threshold momentarily and may be falsely interpreted as a fluid delivery system fault.

Many developments have occurred in the analysis of the pressure existing in the fluid delivery conduit to detect fluid faults. For example, flow perturbations have been used to determine fluid delivery system status based on the pressure response to those perturbations. Other flow patterns have been applied for the purpose of generating a larger pressure response signal to determine fluid line status. However, problems of offset pressure and slow response times to low flow rates still exist in addition to the adverse effect some of these techniques have on flow uniformity.

As has been noted in U.S. Pat. No. 4,898,576 to Philip, the measure of the resistive part of the fluid line impedance can be used to monitor the condition of the fluid line. One technique used in actively monitoring the resistance, rather than merely waiting for pressure to build up, is the alteration of the flow rate. The change in the pressure over the change in the flow rate has been found to accurately indicate the resistive part of the fluid impedance in the system when adequate time is allowed for the pressure to reach equilibrium at each rate. This technique has been found to be effective at higher flow rates with their accompanying higher pressures. A change in these higher flow rates is accompanied by a rapid and measurable change in pressure. Because of the rapid pressure response to the flow rate changes, the flow rate can be varied about the selected flow rate without any significant clinical effect on flow uniformity.

However, at lower flow rates, the clinical requirement of flow rate uniformity restricts the magnitude of the perturbation that can be imposed on the fluid line. It is thus undesirable to alternate between different flow rates to obtain different pressure responses for determining resistance due to the detrimental effect on flow uniformity the flow changes would have as well as the relatively long length of time required to obtain those pressure responses.

Because pressure is used in determining resistance, unknown pressure offsets can have an undesirable effect of making accuracy in resistance estimates difficult to obtain. Additionally, other factors, such as those caused by other pumps impressing flow and resulting pressure responses on the fluid line, can result in inaccuracy in resistance measurement. Some increased immunity to such other factors is desirable as well as a means for compensating for offset pressure.

A further consideration in monitoring fluid line status is the update rate of the information presented. In the case where averaging or other techniques are used in processing pressure data, the update rate may be relatively slow at low flow rates. However, it would be desirable to reduce the delay so that more current data is available to detect faults in the fluid line.

Hence, those skilled in the art have recognized a need for a fluid delivery monitoring system that can detect a fluid delivery fault condition faster than prior systems at low flow rates and that can compensate for the existence of offset pressure while maintaining clinically acceptable flow patterns. Additionally, it has also been recognized that there is a need for a system that is less sensitive to other sources of pressure changes in the conduit such as those caused by other pumps on the same fluid line. It is further desirable to have a data update rate that can assist in detecting an adverse situation faster than the patient's physiological response to the drug being infused. The present invention fulfills these needs and others.

SUMMARY OF THE INVENTION

Briefly and in general terms, the present invention is directed to a system that monitors the impedance to flow in a fluid supply system. In a fluid delivery system in which a flow control device acts on a fluid conduit to control the movement of fluid through the conduit, the flow having a flow waveform, the system for monitoring the impedance to flow comprises a pressure sensor coupled to the conduit for providing pressure signals in response to the pressure sensed in the conduit, and a processor that receives the pressure signals, processes those pressure signals with the flow waveform and determines the impedance to flow based on said processing.

In a further aspect, the processor extracts the resistance from the determined impedance, provides display signals to a display device indicative of the resistance, and the system displays that resistance. Such impedance measurement, extraction of resistance, and display of resistance may occur continuously.

In more detailed aspects, the processor applies a parameter estimation technique to the pressure signals and the flow waveforms in accordance with a predictive model to determine the impedance. A least squares estimate fit to the predictive model is used in one aspect to determine the impedance. The coefficients forming a part of the model are then used to determine the resistance to flow in the system. In another aspect the impedance may be determined by deconvolving the measured pressure signals by the flow waveform. In a further detailed aspect, a linear predictive model is used.

In another aspect, the processor controls the flow control device to cause flow to vary about a selected flow rate in accordance with a predetermined pattern of variation within a predetermined time frame to improve signal processing. The processor then decodes the received pressure signals based on the random flow pattern and processes the decoded pressure signals with the flow waveforms to determine the impedance to flow.

In yet a further aspect, the processor reconstructs a pressure signal from the determined impedance, compares the reconstructed pressure signal to the actual received pressure signal and measures the difference between the two. If the difference between the two exceeds a predetermined threshold, the processor provides a low quality indicator. The display of resistance may be altered by the low quality indicator and alarms may be provided to the operator. In an extreme case, the pumping action may be stopped.

In yet a more detailed aspect concerning the quality of the determined impedance estimation, the coefficients generated from the model used in determining the impedance are compared to predetermined ranges. Based on those coefficients falling inside or outside those ranges, a quality indicator is assigned. Should the quality indicator indicate poor quality, the resistance display may be altered and alarms given.

In a further aspect, the processor applies different impedance measurement techniques depending on the selected flow rate. Where the selected flow rate exceeds a threshold, the processor controls the flow control device to cause a plurality of different flow rates to exist in the conduit. Each flow rate has a flow waveform. The processor then processes the difference in the pressures and the difference in the flow rams to determine the impedance to flow. However for flow rates selected by the operator that are equal to or under the threshold, the processor processes those pressure signals with the flow waveform and determines the impedance to flow based on said processing.

In a further detailed aspect, the processor receives the pressure signals but discards any pressure signal resulting from a predetermined part of the flow control device's cycle of action on the conduit and replaces the discarded pressure signal with another pressure signal resulting from a different part of the control device's cycle. The substitute pressure signal in another aspect comprises a previous pressure signal.

In another aspect, when a predetermined pattern of flow variation is used, the impedance calculation update rate is improved by the use of multiple pressure signal decoders. Multiple decoders are shifted in time to provide new pressure waveform data at an effectively increased data rate.

Other aspects and advantages of the invention will become apparent from the following detailed description and the accompanying drawings, which illustrate by way of example the features of the invention.

BRIEF DESCRIPTION OF THE DRAWINGS

FIGS. 3, 4 and 5 are diagrams showing the encoding of the fluid flow with a code length of seven bits, the pressure responses to the encoded fluid flow, and the decoding of the pressure responses into a composite signal;

DETAILED DESCRIPTION OF THE PREFERRED EMBODIMENTS

Figure 1:
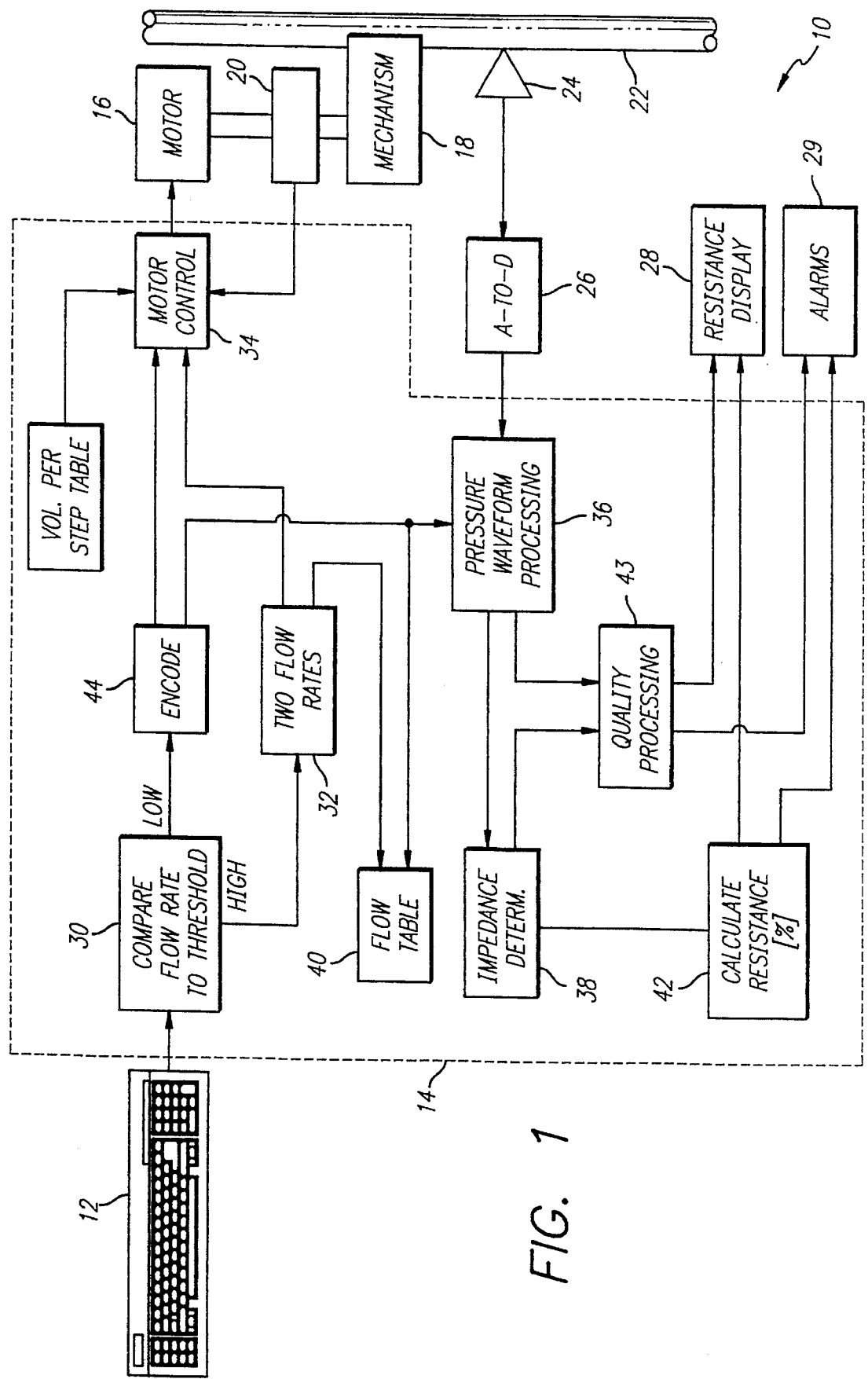
FIG. 1 is a block schematic diagram of a fluid delivery and monitoring system embodying features of the invention.

Referring now to the drawings with more particularity, wherein like reference numerals in the separate views indicate like or corresponding elements, there is shown in FIG. 1 a block diagram of an impedance monitoring system 10 incorporating aspects of the current invention. The impedance monitoring system is coupled to the conduit 22 of a fluid delivery system in which a motor 16 drives a pumping mechanism 18 that operates on the conduit 22 to move fluid through the conduit 22.

A user input device 12, such as a keypad, provides operator instructions, such as flow rate selection, to a processor 14. The processor 14 controls the operation of the motor 16 driving the pumping mechanism 18 which in this case comprises a series of peristaltic fingers arranged in a linear relationship and moved by a rotating cam shaft coupled to the motor 16 output shaft. A motor position sensor 20 determines the position of the motor 16 and pumping mechanism 18 and provides a position signal to the processor 14. Located downstream from the pumping mechanism is a pressure sensor 24 coupled to the conduit 22 to sense pressure in the conduit. An analog-to-digital converter 26 ("A-to-D") receives the analog pressure output signals from the sensor 24 and converts them to a digital format at a particular sample rate controlled by the processor 14. The processor 14 receives the digital pressure signals, processes them as described in more detail below and calculates the impedance to flow in the system. From the impedance, the resistance to-flow is determined. A display 28 presents the resistance. Alarms 29 are provided to indicate an unsatisfactory resistance level.

The selection of a flow rate is made at the keypad 12 and is received by the processor 14 to compare 30 against a threshold to determine if the selection is a "high" flow rate or a "low" flow rate. A threshold, such as fifty milliliters per hour is used in one case. A selected flow rate exceeding this rate is considered high and at or below this rate is considered low.

As one aspect of the impedance measuring system shown in FIG. 1, two different approaches to determining the fluid system impedance are used so that a wide range of flow rates may be provided by the fluid delivery system with continuous, accurate impedance determination. For high flow rates, a "bi-rate" approach is used where the flow rate is varied and the responsive pressure signals are monitored. In this approach, the changes in pressure and flow are used to directly determine resistance.

For low flow rates, the flow is also varied but in accordance with a predetermined pattern of variation about the selected rate. The pressure signals are decoded in accordance with the predetermined pattern of variation and the resulting decoded pressure signals are processed with the flow waveform to determine the impedance. Resistance is then determined from the impedance and is displayed in a percentage in one embodiment.

In the event that a high flow rate is selected, the processor 14 controls 32 the motor to run at two or more different flow rates. The flow rate commands are provided to the motor controller 34 which in turn causes the motor 16 to act on the conduit 22 through the mechanism 18 to pump fluid through the conduit 22 at those discrete rates. The rates are selected in one embodiment to average to the selected flow rate for the purpose of maintaining flow uniformity.

Varying the flow rate at relatively high flow rates causes a rapid pressure response as discussed above and the resistance to fluid flow of the system can be determined relatively rapidly in accordance with the following:

$$R = \frac{P_2 - P_1}{F_2 - F_1}$$

where:
R=resistance
$F_1$=first flow rate
$F_2$=second flow rate
$P_1$=pressure at the first flow rate
$P_2$=pressure at the second flow rate Another relationship that may be used in determining a resistance percentage and that takes into account the sample rate is:

$$R\% = \left(\frac{1}{15}\right) \frac{\frac{\sum_{j=0}^{M-1} P_{hi}(j)}{M} - \frac{\sum_{k=0}^{N-1} P_{lo}(k)}{N}}{F_{hi} - F_{lo}}$$

where:
R %=resistance percentage where 100% equals a calculated resistance of 1500 fluids ohms.
P=pressure in mm Hg
F=flow in liters per hour
M=samples in one revolution at the high rate
N=samples in one revolution at the low rate The pressure responses to the flow waveforms in the conduit 22 are monitored by the pressure sensor 24 with digital pressure signals provided to the processor 14 by the A-to-D converter 26. Those pressure signals may be filtered or otherwise processed 36 and are then divided by the flow 38 to determine resistance as shown above. The two flow rates that were selected 32 are provided to the flow table memory 40 which makes available the particular flow quantities pumped by the mechanism for each pressure sample. The difference between the pressures at the two flow rates is divided by the difference between the flow quantities at the two flow rates (as per the first equation above). The resulting quotient is used by the processor 14 to calculate resistance 42. This resistance percentage is displayed 28.

Therefore, above the threshold flow rate, in this case fifty milliliters per hour, multiple flow rates are applied to the fluid conduit and the changes in the pressures resulting from these flow rates are used to directly calculate resistance. The flow rates selected and the length of time that they are each applied are based on averaging to the selected flow rate so that there is no significant clinical effect by altering the flow rates.

However at a selected flow rate that is considered to be "low," for example 1.0 milliliter per hour, the alteration of flow rates about the selected rate to achieve significant and rapid changes in conduit pressure is typically not feasible, as discussed above. In this case, a different approach is used to determine the impedance of the fluid flow system.

The pressure signals received reflect the effects of the fluid flow impedance of the delivery system on that pressure. That impedance includes a real component; i.e., resistance, as well as other components, such as compliance and the inertance of the system. The impedance is thus the transfer function in this case between the flow and the pressure. In order to accurately obtain the resistance of the system, the transfer function, or impedance, may be determined from the flow and pressure waveforms. The system discussed below and shown in the accompanying drawings presents a system for determining that impedance from sensed pressure signals.

In the case where the selected flow rate is considered a "low" rate 30, the processor 14 outputs a "low flow" signal to an encoder 44. The encoder 44 provides coded motor drive signals to the motor control 34 to establish a varying flow pattern through the conduit 22 about the selected flow rate. Such a pattern in one embodiment takes the form of a pseudo-random binary code sequence ("PRBS") that causes flow to occur in a predetermined pattern of variation over a predetermined time frame having multiple time periods in the frame. However, the pattern repeats for subsequent time frames.

The digital pressure samples from the A-to-D converter 26 are sampled and decoded 36 in accordance with the predetermined pattern of flow variation provided by the encoder 44. Filtering, decimating, and other processing techniques may be applied here as is discussed below. The decoded pressure signals are then processed with the flow waveform 38 for determination of the impedance of the system to flow. A flow waveform corresponding to the flow rate selected is retrieved from the flow table 40 and is processed with the pressure to determine the impedance based on a predetermined relationship or model of flow and pressure for the system. The resulting impedance is then used to calculate 42 the resistance of the system to flow and is displayed 28 as in the high flow rate case discussed above. This process is discussed in more detail below.

A quality processor 43 monitors the impedance determination and controls the resistance display and alarm in the event that the quality of the impedance estimation is deemed to be poor.

Figure 2A:
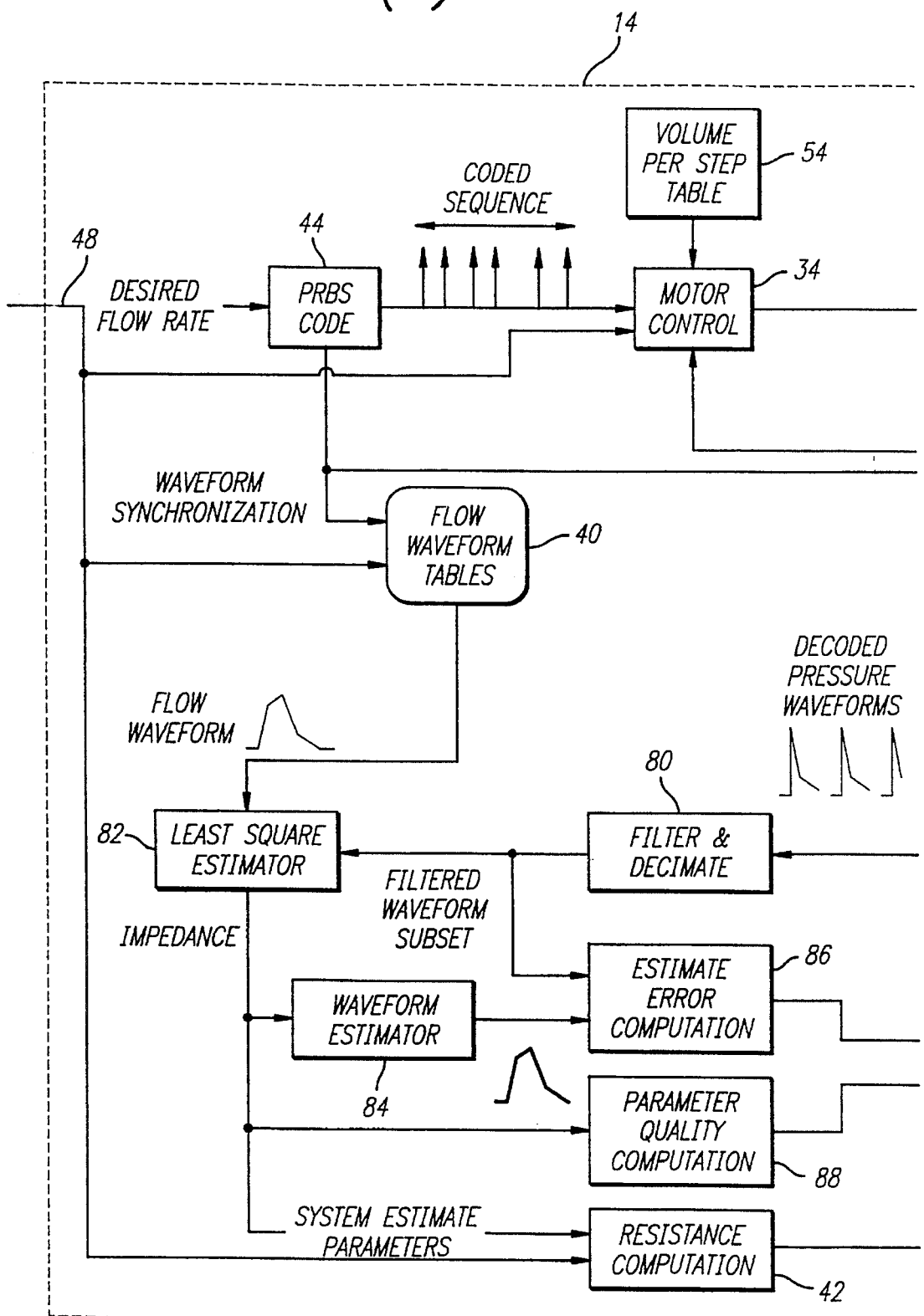
FIG. 2 is a more detailed block diagram of a fluid delivery and monitoring system embodying further features of the invention for sensing impedance and determinng resistance at low flow rates.
Figure 2B:
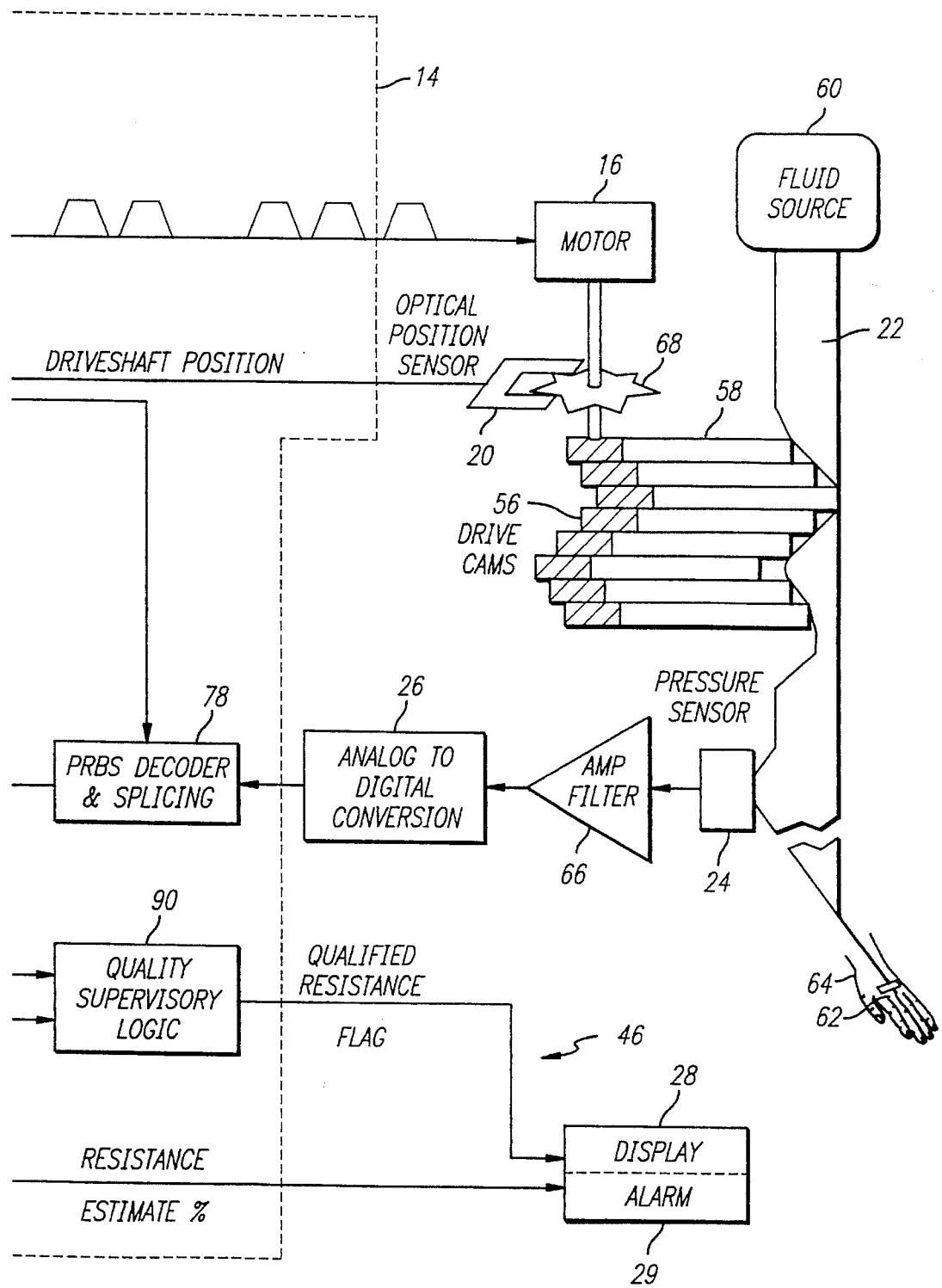

Referring now to FIGS. 2 and 3, a more detailed embodiment of a system 46 is presented for operation at "low" flow rates. The flow rate selection 48 is received by the encoder 44 which in this case, is a PRBS encoder. In response to the input signal 48, the PRBS encoder 44 outputs a PRBS code to the motor controller 34 to cause varying flow in accordance with the code or pattern. In this embodiment, the PRBS code comprises a predetermined sequence of ones and zeros (flow and no flow signals) of length $M=2^n-1$, where "n" is 3, 4, or 5 in this embodiment.

It takes longer to receive thirty-one time periods of data than it does to receive seven time periods of data. As a general goal, it is desirable to have the measurement period approximately the same for all flow rates. Therefore, the code length is shortened for lower flow rates and lengthened for higher flow rates. Additionally, the volume of fluid that flows in response to each bit of the code can be altered to achieve this goal. There are thus two methods that may be used either alone or in combination to achieve the goal. Thus, at low flow rates, a longer code length is less desirable than a shorter code length due to the long update time. The code length is therefore generally directly proportional to the flow rate selected and in this case, the number of ones is greater by one than the number of zeros. Thus, the greater the flow rate, the longer the code length and conversely, the lower the flow rate, the shorter the code length.

A single code length of seven (m=7, n=3) is shown in FIG. 3. Each bit of the code is assigned a value of either one or zero. The code length is shown occurring in a time frame 50 with multiple time periods corresponding to the bits making up the code length. As shown in the example of FIG. 3, there are four "ones" indicated by the vertical rectangles 52 and three "zeros" occurring in a pseudo-random pattern. In one embodiment, a code length of seven (m=7, n=3) is used for flow rates in the range of 1.05 to 5.04 ml/hr; a code length of fifteen (m=15, n=4) is used for flow rams in the range of 5.05–16.04 ml/hr and a code length of thirty-one (m=31, n=5) is used for flow rates in the range of 16.05–50.00 ml/hr. Other code lengths may be used.

It has been found that the use of a pseudo-random binary code in controlling the pumping action on the conduit can result in rejection of certain type of extraneous pressure signals, thus increasing accuracy in determining the impedance in the line. For example, ambulation of the patient may impose pressure changes in the conduit due to raising or lowering the conduit. The imposition of fluid flow in the conduit from other pumping mechanisms may result in extraneous pressure levels at the pressure sensor. The use of the PRBS approach assists in reducing such extraneous pressure signals in the decoded signal.

In the system shown in FIG. 2, the infusion pump comprises a step motor 16 having an output shaft connected to a cam shaft on which multiple cams 56 are mounted. Each cam moves a respective pumping finger 58 that translates the rotary motion of its respective cam 56 into linear motion. Each finger 58 presses against the conduit 22 to cause fluid to move through the conduit in a downstream direction.

The step motor 16 and the cams 56 mounted to it move in steps or "increments." A position-indicating disk 68 is also mounted to the output shaft of the motor 16 and when coupled with an optical sensor 20, provides a position signal indicative of the position of the cam shaft.

Each incremental movement of the output shaft of the motor 16 and consequent incremental movements of the pumping fingers 58 result in the pumping of a volume of fluid through the conduit 22. These volumes may be measured by means familiar to those skilled in the art; for example, gravimetric measurement, and those volumes correlated with each position of the motor output shaft and stored in a memory 54.

The conduit is shown connected between a fluid reservoir 60 and a needle 62 inserted in a patient 64. The conduit is flexible in nature and may take the form of a tubing or may be part of a dedicated pumping segment.

The pressure sensor 24 is coupled to the conduit 22 and monitors the pressure existing in the conduit 22 between the infusion fingers 58 and the patient's blood vessel and produces pressure signals representing the detected pressure. The pressure signals are analog and are amplified and filtered, such as by a 20 Hz low pass filter 66 before being provided to the analog-to-digital converter 26. Such amplifying, filtering, and conversion to a digital signal may be performed in other ways and may all be built into the sensor 24 itself in a different embodiment.

In response to the PRBS code, control signals are provided to the motor 16 by the motor control 34 to cause the motor to act on the conduit according to the code. The flow waveforms resulting from PRBS code bits can be estimated by means familiar to those skilled in the art and stored in the flow waveform table 40. While the volume-per-step table 54 and flow waveform table 40 are shown as separate blocks in FIG. 2, they may in fact reside in the same memory available to the processor 14 (FIG. 1).

The digitized pressure signal is then decoded in accordance with the PRBS signal. In accordance with the embodiments shown in FIGS. 2 through 5, the pressure waveforms over the entire code length/time frame 50 (FIG. 4) are decoded into a single time period or bit 70 equal in length to a single time period in the time frame 50 (FIG. 5) followed by M–1 time periods of zeros. As shown, the amplitude of the pressure waveform is greatly increased while the length remains the same as any single pressure waveforms in the time frame 50. Thus in the case shown in FIGS. 3–5, the time frame consists of seven time periods, thus the single composite pressure waveform has four times the amplitude of each waveform in the time frame 50. Where each pressure waveform has an amplitude of three units, the composite waveform shown in FIG. 5 has the amplitude of twelve units, as shown.

Figures 6, 7:
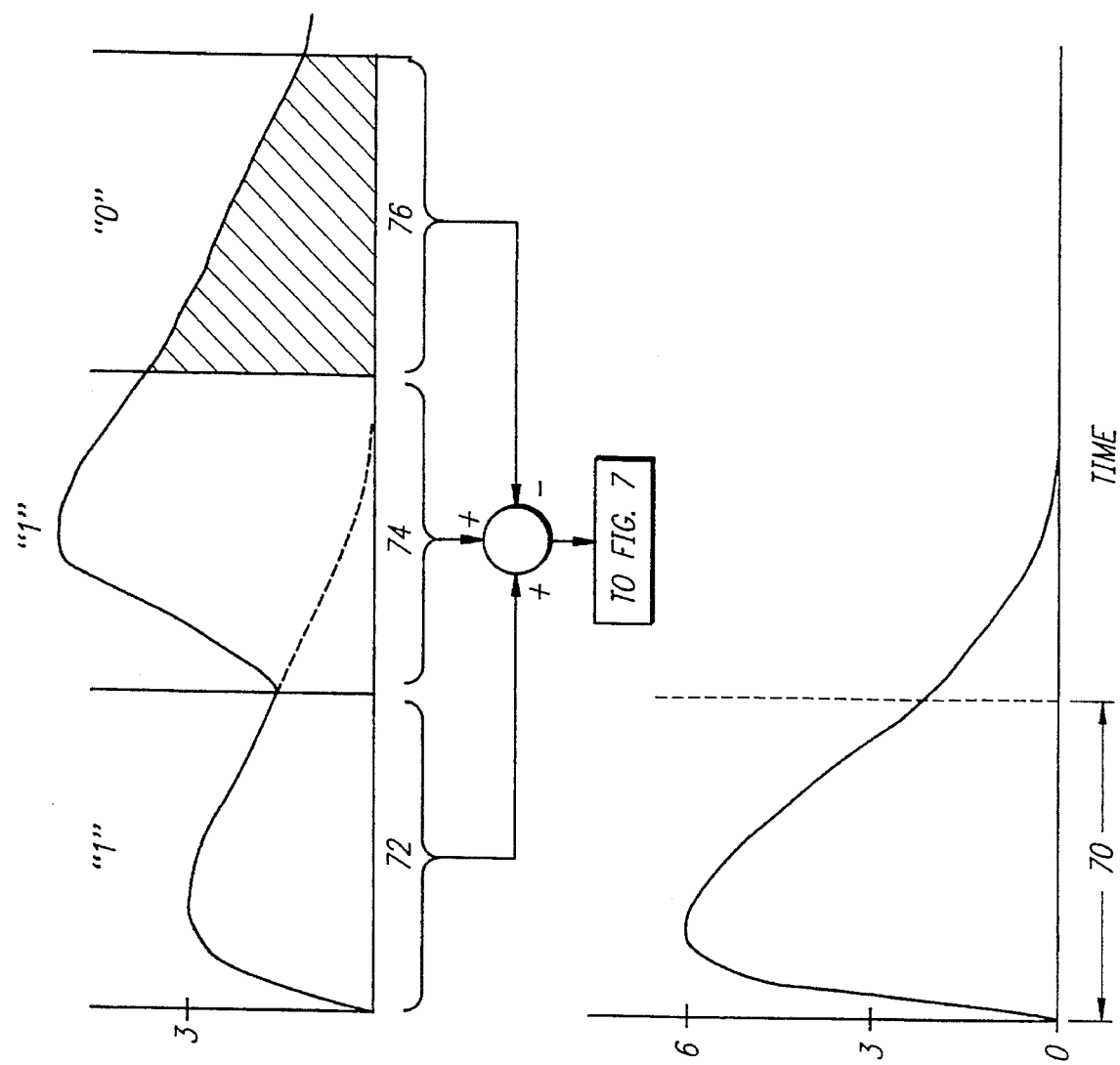
FIGS. 6 and 7 graphically illustrate the decoding of ones and zero pressure waveforms into a composite waveform.

Referring now to FIGS. 6 and 7, the process of decoding 78 the pressure waveform of a code length into the composite pressure waveform is shown. Only three time periods from the time frame 50 of FIG. 3 are shown. In the first two periods, 72 and 74, a "one" PRBS code was provided to the motor and in the third period 76 a "zero" was provided to the motor. However, pressure exists in all three time periods 72–76, and pressure overlap from the first period exists in the second time period 74. The pressure in each of these periods 72–76 is combined as schematically shown in FIG. 6 such that pressure existing in a "ones" time period is added while pressure existing in a "zeros" time period is subtracted. Thus the pressures in the first two time periods 72 and 74 are added to each other while the pressure in the third time period 76 is subtracted from the others. This results in the composite waveform shown in FIG. 7. Thus any pressure in the "zeros" time periods is subtracted from the composite reducing the possibility of overlapping of sequential pressure responses and producing a response waveform equivalent to one spaced at the full code period 50.

Additionally, the pressure signals are "spliced" 80 in this embodiment. As is known to those skilled in the art, linear peristaltic pump cycles include a portion of equalizing flow resulting from the most downstream finger retracting and exposing the downstream fluid line to the pressure between this retracting finger and a more upstream finger already in place occluding the tubing. The equalization pressure flow that results may involve some negative flow and pressure. At other times it may not. Additionally, the motor is sped up during this time to traverse this portion of the cycle as quickly as possible ("speed-up cycle"). Because of this uncertainty as to the possibility of negative flow, and the speed-up portion of the pump cycle, including this portion of the pressure wave in the determination of the pressure in the fluid conduit could skew the results unless fairly complex processing techniques are applied.

However, this portion of the fluid flow cycle of the peristaltic pump can be identified by the position detection sensor 20 and therefore the pressure response attributable to this cycle portion can likewise be identified. In the splicing feature in accordance with the invention, this portion of the pressure wave is discarded and replaced by the pressure samples in the time period containing the last non-zero pressure response waveform. Thus, the speed up cycle waveform is edited out while the last waveform is spliced in. The remaining pressure waveforms are offset to remain contiguous with the last sample of the spliced waveform. It has been found that this results in less processing time requirements and a more accurate view of the actual pressure response in the system during the normal fluid movement parts of the pumping cycle.

The decoded and spliced waveform is then filtered and decimated 80. The pressure waveform is low-pass filtered, for example at 4 Hz. This additional filtering reduces the complexity of the model required for determining impedance.

Figure 8:
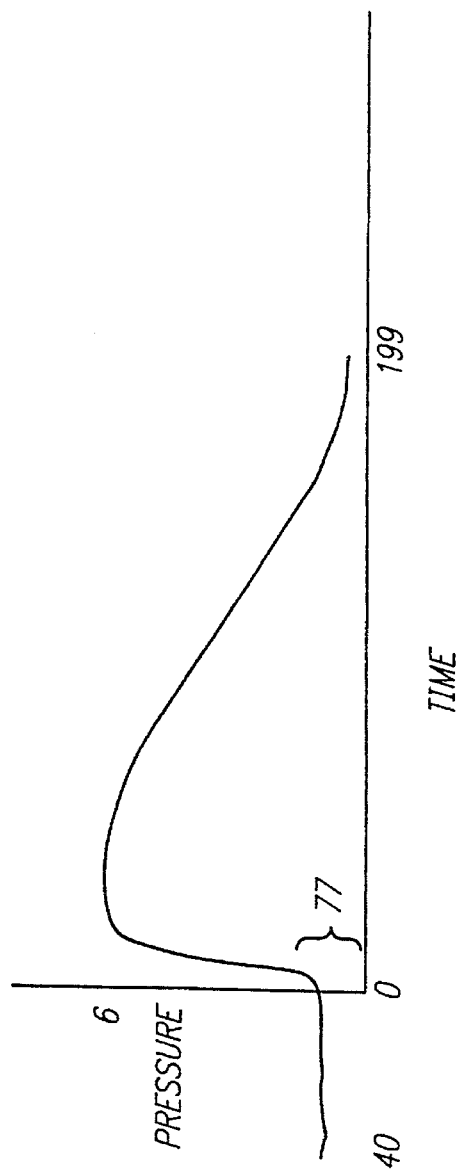
FIGS. 8 and 9 graphically illustrate a decimated and shifted decoded pressure waveform in which offset pressure can be subtracted.
Figure 9:
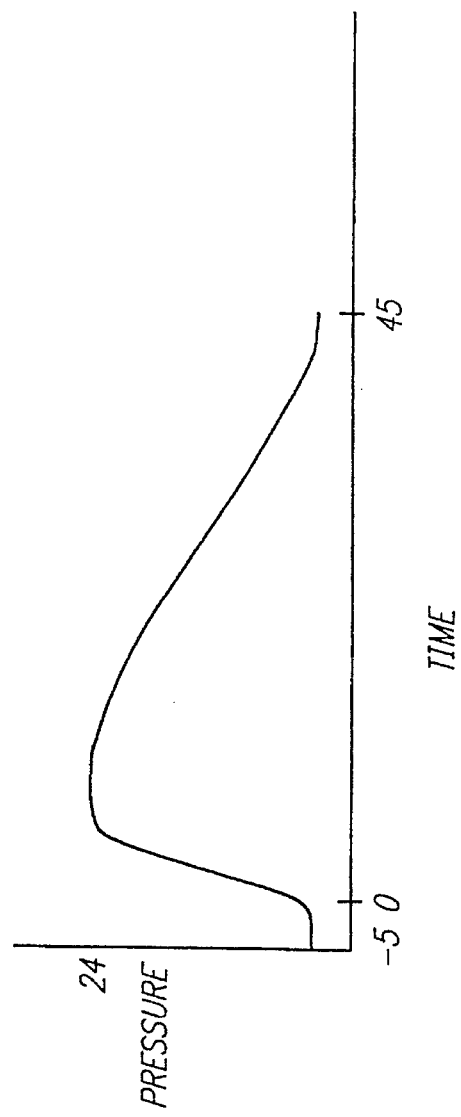

Additionally, the pressure waveform is shifted as shown in FIGS. 8 and 9 for removal of offset pressure caused by head height or other factors. Although shown in FIG. 7 as decaying to the zero value of pressure, there may actually remain some offset pressure 77, as shown in FIG. 8. The pressure waveform comprises two-hundred samples starting at zero and extending to one-hundred and ninety nine. However, the waveform is not at zero amplitude at the first sample. In the embodiment shown, the pressure waveform is shifted to include certain samples from the previous waveform. FIG. 9 presents the case where twenty samples from the previous waveform have been included in the present waveform. The mean pressure of the twenty samples is considered to be the offset pressure. Prior to low pass filtering and decimation 80, this amount of pressure is subtracted.

Additionally the present waveform that has had the offset subtracted and has been filtered, has been averaged and decimated from a ratio of 4 to 1. That is, every four samples have been summed into one sample. Thus only fifty samples of the two hundred remain to represent the pressure waveform. The decimation process yields the advantage of a limited low pass filtering in addition to reducing the processing time needed to determine resistance. Decimation is not required but has been found to be an effective tool for increasing processing speed.

The filtered and decimated pressure waveform is then applied to the model to determine the impedance in the system. In one embodiment, a predictive model of the relationship between flow and pressure was used to determine the impedance as follows:

$$P(k) = a_1 P(k-1) + a_2 P(k-2) + b_1 F(k-1) \qquad (1)$$

where:
 k=the sample index
 P=pressure sample
 F=flow sample
 a, b=coefficients

There are three coefficients in the above model, two of which relate to pressure and one of which relates to flow. In determining the coefficients, a least squares estimator 82 was used. By techniques well known to those skilled in the art, the estimator 82 determines the coefficients $a_1$ and $a_2$ from an analysis of the actual pressure waveform and $b_1$ from the stored flow waveform table to most closely represent that received pressure waveform.

Upon determination of the coefficients $a_1$, $a_2$, and $b_1$, the transfer function or impedance relationship between the flow and pressure signals has been determined. The impedance can then be analyzed to determine various system characteristics. In this case, the resistance to fluid flow is determined.

The coefficients $a_1$, $a_2$, and $b_1$ are provided to the resistance computation block 42 for the actual calculation of resistance. Rearranging the terms of equation (1) results in:

$$P(k) - a_1 P(k-1) - a_2 P(k-2) = b_1 F(k) \qquad (2)$$

The above simplifies to:

$$R(j) = \lim_{k \to \infty} \frac{P(k)}{F(k)} = \frac{b_1}{1 - a_1 - a_2} \qquad (3)$$

where:
 j=the resistance index

The calculated resistance is then divided by the maximum resistance (currently defined as 1500 fluid ohms) to determine the resistance percentage. The maximum displayed resistance percentage is 100 percent in this case. The percentage is provided to a display 28.

It should be noted that more complex models could be used; however, additional computational time would be needed to determine the transfer function. It has been found that the model expressed above resulted in accurate impedance measurements while reducing the requirements on the processor. Additionally, other parameter estimation techniques may be used. For example, a computational neural network may also function acceptably. Also, flow waveforms have been described and shown herein as being stored. In another embodiment, they may actually be measured in real time and provided for processing with the pressure signals as described above.

In addition, FIG. 2 discloses a system for determining the quality of the resistance measurement. In some cases, the quality of the pressure waveforms received from the conduit 22 may be too low to obtain an accurate measure of resistance regardless of their being filtered, decoded, and spliced. Identification of such poor quality waveforms is made by the quality system disclosed below so that spurious resistance measurements are identified, and in extreme cases, are not provided to the operator of the equipment.

In the embodiment shown, the filtered and decimated pressure waveform is compared against a pressure waveform synthesized from the a and b coefficients generated by the least square estimator 82 and the flow waveform 40. A waveform estimator 84 receives the coefficients and synthesizes a pressure waveform. That synthesized waveform is compared on a sample-by-sample basis to the actual pressure waveform by the error estimator 86. The absolute values of the differences are summed. That sum is compared against ranges and a quality number assigned. In this embodiment, no differences would yield a quality number of "0". A sum of differences exceeding thirteen would be assigned a quality number of "2" and a sum between five and thirteen would be assigned a quality number of "1".

A second part of the quality system involves a review of the coefficients themselves. A parameter quality estimator 88 compares each of the coefficients $a_1$, $a_2$ and $b_1$ to predetermined ranges. A quality number of "0" is assigned where the coefficients fall within a first range. As in the first part of the quality system, quality numbers of "1" and "2" are assigned for coefficients falling in different ranges indicating successively poorer quality.

Both the waveform quality number and the parameter quality number are supplied to a quality supervisor 90 that outputs a control signal to the display 28 if the quality is too low. In the extreme case where the integer mean of the two quality numbers is "2" for three consecutive resistance estimates, the quality control supervisor 90 will blank out the resistance display 28 of the numerical value and the bar chart and will provide an indication that conditions are such that an accurate resistance display cannot be generated. When the integer mean is "0" or "1", the quality supervisor does not change the displayed resistance value.

Also within this module is detection of resistance percentages greater than or equal to 100%. The first time this occurs, the resistance display shows "resistance alert." After three consecutive resistance percentages greater than or equal to 100%, the pump will go into an occlusion alarm mode.

Figures 10, 11:
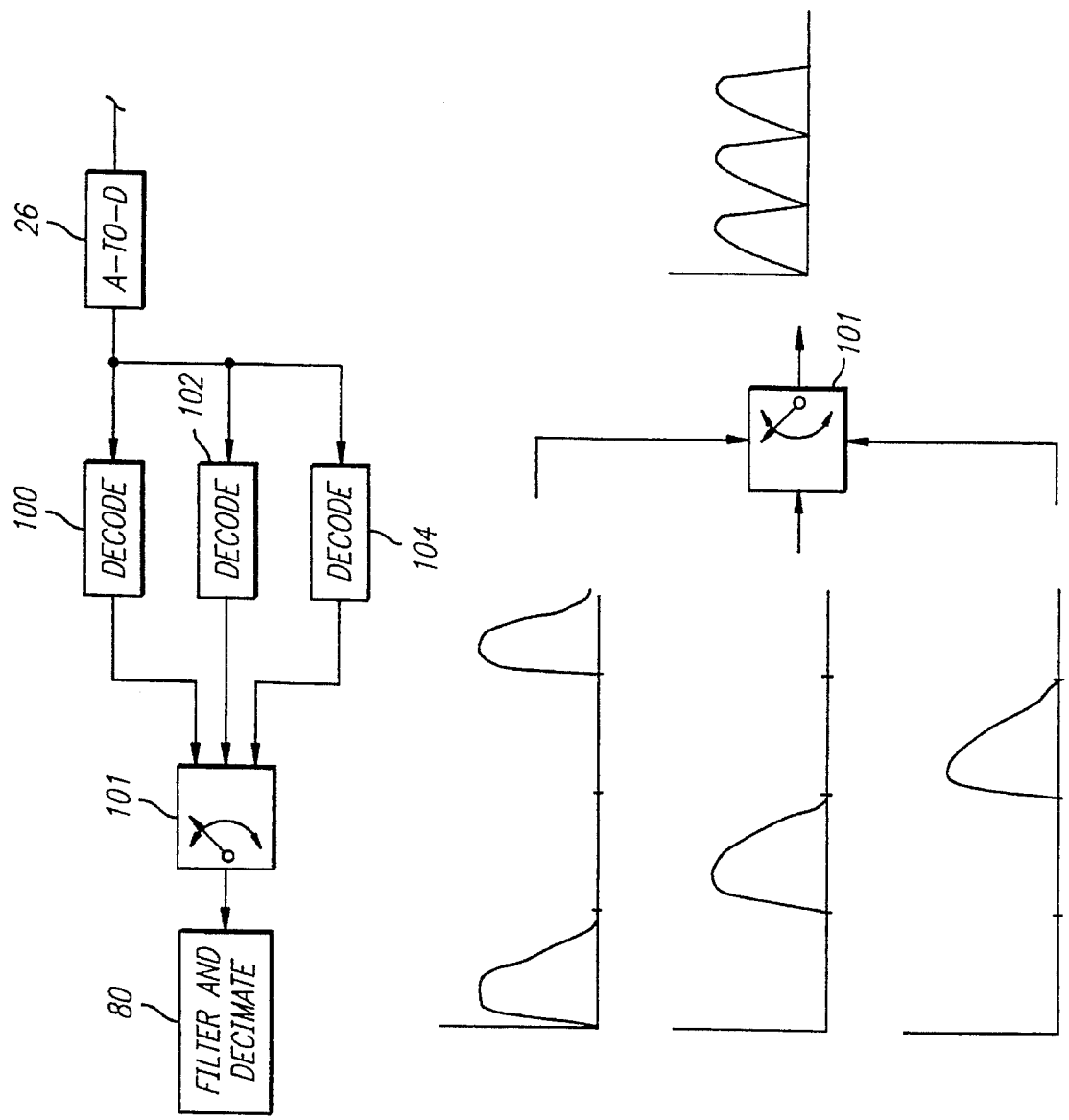
FIGS. 10 and 11 present an embodiment where three decoders are used to provide an increased update rate of pressure data.

In some cases, particularly at low flow rates, the update rate of the resistance calculation may not be as fast as desired. In the embodiment shown in FIGS. 10 and 11, a system is disclosed for increasing the speed of updating the resistance calculation. In the embodiment shown in FIG. 10, three PRBS decoders are used that are shifted in time to provide more frequent updates of the decoded pressure waveform. They are switched into the filter and decimation 80 block sequentially by a switch 101. In one embodiment, the resistance estimates were required every ten seconds. At low flow rates, decoded pressure waveforms could be updated infrequently, for example, only every thirty seconds. Each decoder 100, 102, 104 was shifted by ten seconds. Thus each decoder would overlap the other with twenty seconds of input pressure data but the three decoders would possess new decoded pressure data every ten seconds. The effect is shown in FIG. 11. The top decoder 100 provides a first pressure waveform; ten seconds later, the middle decoder 102 provides a second pressure waveform, and ten seconds later, the bottom decoder 104 provides a third waveform. All decoders 100, 102, and 104 operate on the same data and their outputs are sequentially switched into the filter 80.

Figure 12:
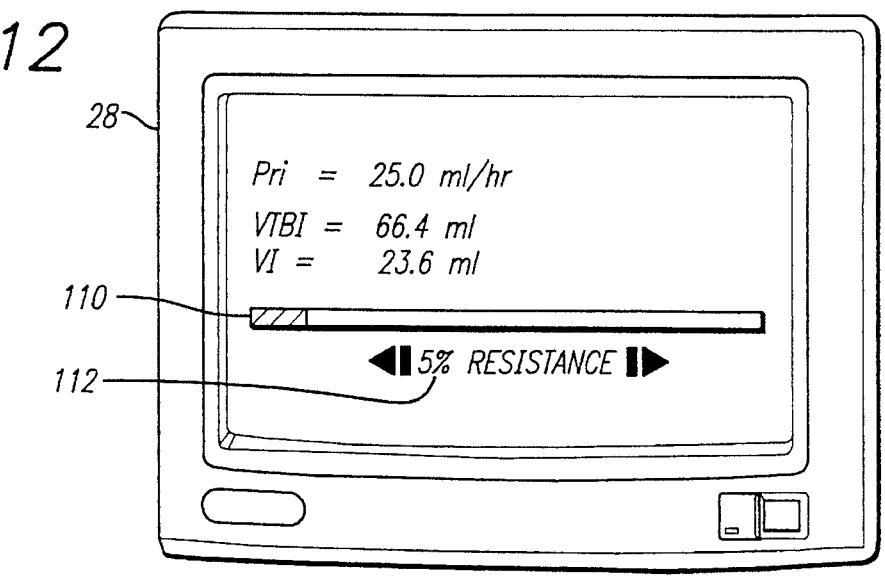
FIGS. 12, 13, and 14 are examples of displays usable to present the resistance to flow encountered in a fluid delivery system.
Figure 13:
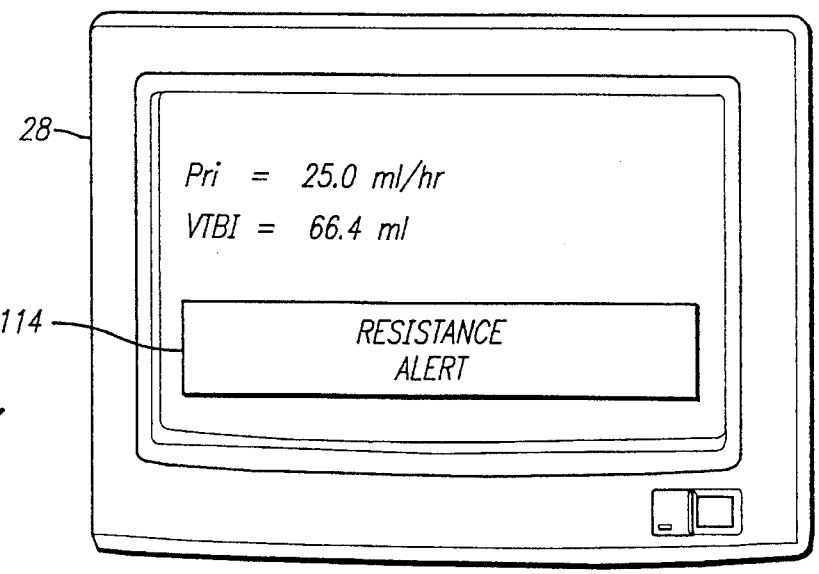

Referring now to FIGS. 12 and 13, examples of resistance displays are provided. The system in accordance with the invention both calculates and displays resistance percentage continuously. The resistance displays may be altered in dependence on the conditions experienced by the infusion system, but some display of the resistance status is always displayed while the pump is operating. For example, FIG. 12 presents a typical display when an infusion is progressing normally. The display 28 includes a graphic display 110 of resistance as well as a text display 112. Under the present infusion conditions, a resistance measurement display occurs continuously. However, in the case where the quality supervisor 90 (FIG. 2) determines that the resistance calculation quality is poor, a text display of "- -" may appear. This warning text may persist until conditions change so that a resistance calculation can once again be displayed or until the processor terminates the infusion. As discussed above, in the case where the resistance equals or exceeds 100%, the display may provide the text "Resistance Alert" as shown in FIG. 13. After a predetermined number of alerts, such as three, the pump goes into occlusion alarm. Additionally, audible signals may be used to also communicated information to the infusion system operator. An audible signal, such as a first tone, may be presented in the case where the resistance exceeds a certain level. An audible signal of a different tone may be presented where the quality of the signal is too poor to present an accurate measurement. Other types of audible and visual signals may be used to communicate information concerning the resistance measuring results of the system.

Figure 14:
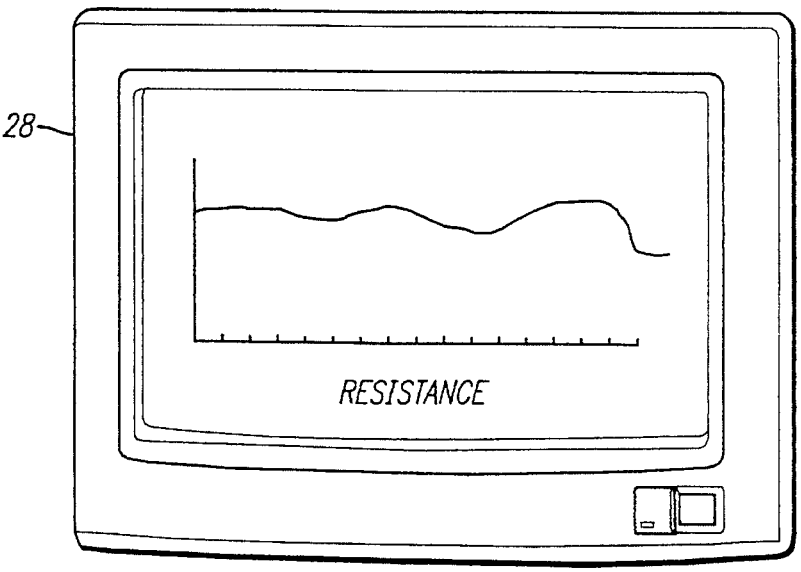

FIG. 14 provides another type of resistance display. In this case a resistance trend is presented. Other types of displays are possible.

Although specific embodiments of the invention have been described and illustrated, it is clear that it is susceptible to numerous modifications and adaptations within the ability of those skilled in the art and without the exercise of inventive faculty. Thus, it should be understood that various changes in form, detail and use of the present invention may be made without departing from the spirit and scope of the invention.

What is claimed is:

1. A system for monitoring impedance to flow in a fluid delivery system in which a flow control device acts on a fluid conduit to control the flow of fluid through the conduit, the system comprising:

a pressure sensor coupled to the conduit for providing pressure signals in response to the pressure sensed in the conduit;

a memory that provides a flow waveform corresponding to the flow of fluid in the conduit;

a processor that receives the pressure signals and the flow waveform, processes those pressure signals with the flow waveform, determines the impedance to flow based on said processing, and extracts a resistance from the determined impedance; and a display that displays a value representing the extracted resistance.

2. The system according to claim 1, wherein the display comprises a graphic display of the resistance value.

3. The system according to claim 1, wherein the display comprises a text display of the resistance value.

4. The system according to claim 3, wherein the display also comprises a graphic display of the resistance value.

5. The system according to claim 1, wherein the display comprises a display of the resistance trend.

6. The system according to claim 1, further comprising:

a quality processor that determines a quality of the determined resistance; and wherein the display displays an indicia of the determined resistance quality.

7. A system for monitoring impedance to flow in a fluid delivery system in which a flow control device acts on a fluid conduit to control the flow of fluid through the conduit, the flow having a flow waveform, the system comprising:

a pressure sensor coupled to the conduit for providing pressure a signals in response to the pressure sensed in the conduit;

a memory that provides a flow waveform corresponding to the flow of fluid in the conduit;

a processor that receives the pressure signals and the flow waveform and determines the impedance by deconvolving the pressure signals by the flow waveform.

8. A system for monitoring impedance to flow in a fluid delivery system in which a flow control device acts on a fluid conduit to control the flow of fluid through the conduit, the system comprising:

a pressure sensor coupled to the conduit for providing pressure signals in response to the pressure sensed in the conduit;

a memory that provides a flow waveform corresponding to the flow of fluid in the conduit; and a processor comprising a model of the relationship between flow and pressure that receives the pressure signals and the flow waveform, processes the pressure signals with the flow waveform, and determines the impedance to flow based on said processing wherein the processor applies a parameter estimation technique in accordance with the model to determine the impedance.

9. The system according to claim 8, wherein the parameter estimation technique comprises a linear least squares estimate applied to the pressure signals and the flow waveforms.

10. The system according to claim 8, wherein the parameter estimation technique comprises a computational neural network applied to the pressure signals and the flow waveforms.

11. The system of claim 8 wherein the model comprises a linear predictive model.

12. A system for monitoring impedance to flow in a fluid delivery system in which a flow control device acts on a fluid conduit in response to an operator selected flow rate to control the movement of fluid through the conduit, the system comprising:
 a pressure sensor coupled to the conduit for providing pressure signals in response to the pressure sensed in the conduit;
 a flow table memory in which a flow waveform is stored;
 a processor that; should be:
  analyzes the selected flow rate and determines if the flow rate is above or below a threshold;
  if the flow rate is above the threshold, the processor controls the flow control device to cause a plurality of different flow rates to exist in the conduit, receives the pressure signals resulting from each flow rate, and determines the impedance by processing changes in pressure and changes in flow together; and
  if the flow rate is below the threshold, the processor receives the pressure signals, retrieves from the flow table memory a flow waveform corresponding to the selected flow rate, and processes the pressure signals with the flow waveform to determine the impedance to flow.

13. A system for monitoring impedance to flow in a fluid delivery system in which a flow control device acts on a fluid conduit to control the flow of fluid through the conduit, the system comprising:
 a pressure sensor coupled to the conduit for providing pressure signals in response to the pressure sensed in the conduit;
 a memory that provides a flow waveform corresponding to the flow of fluid in the conduit; and
 a processor that:
  controls the flow control device to cause flow in accordance with a pattern of flow variation about a selected flow rate, wherein the pattern of flow variation comprises a pseudo-random binary code;
  receives the pressure signals and the flow waveform;
  decodes the received pressure signals based on the pattern of flow variation; and
  processes those pressure signals with the flow waveform to determine the impedance to flow.

14. The system according to claim 13 wherein:
 the processor provides the pseudo-random binary code signals within a predetermined time frame with the predetermined time frame divided into a plurality of time periods, the pseudo-random binary code signals synchronized with the time periods; and
 the processor decodes the pressure signals received within each time period of the predetermined time frame to result in a single pressure waveform for the entire predetermined time frame.

15. The system according to claim 14 wherein the processor adds the pressure waveforms in those time periods in which the pseudo-random binary code issued a pump signal and subtracts the pressure waveforms detected in those time periods in which the pseudo-random binary code did not issue a pump signal to form the single pressure waveform.

16. The system according to claim 15 wherein the processor combines the pressure signals received from a previous time frame with at least some of the pressure signals from the current time frame to result in the single pressure waveform.

17. A system for continuously monitoring impedance to flow in a fluid delivery system in which a flow control device acts on a fluid conduit to control the movement of fluid through the conduit, the flow having a flow waveform, the system comprising:
 a display device;
 a pressure sensor coupled to the conduit for continuously providing pressure signals in response to the pressure sensed in the conduit;
 a processor that:
  receives the pressure signals;
  continuously processes those pressure signals with the flow waveform and continuously determines the impedance to flow based on said processing;
  extracts the resistance from the determined impedance;
  continuously provides display signals to the display device indicative of the resistance measurement;
 wherein the display device displays an indication of the measured resistance.

18. A system for monitoring impedance to flow in a fluid delivery system in which a flow control device acts on a fluid conduit to control the movement of fluid through the conduit, the flow having a flow waveform, the system comprising:
 a pressure sensor coupled to the conduit for providing pressure signals in response to the pressure sensed in the conduit;
 a processor that:
  receives the pressure signals, processes those pressure signals with the flow waveform and determines the impedance to flow based on said processing;
  reconstructs a pressure signal from the determined impedance;
  compares the reconstructed pressure signal to the received pressure signal and measures the difference between the two;
  provides a low quality indicator in the event that the difference between the reconstructed pressure signal and the received pressure signal exceeds a predetermined threshold.

19. A system for monitoring impedance to flow in a fluid delivery system in which a flow control device acts on a fluid conduit to control the movement of fluid through the conduit, the flow control device having a movement cycle with a first portion, the flow having a flow waveform, the system comprising:
 a pressure sensor coupled to the conduit for providing pressure signals in response to the pressure sensed in the conduit;
 a processor that:
  receives the pressure signals;
  discards pressure signals occurring in response to the first portion of the flow control device cycle;
  substitutes other pressure signals for the discarded pressure signals; and
  processes the remaining pressure signals with the flow waveform to determine the impedance to flow based on said processing.

20. The system according to claim 19 wherein the processor substitutes previously received pressure signals for the discarded signals.

21. A system for determining flow impedance in a fluid delivery assembly in which a flow control device acts on a fluid conduit to control the flow of fluid through the conduit, wherein the flow control device provides a selected flow waveform in the fluid flowing through the fluid conduit, the system comprising:

a pressure sensor coupled to the conduit for providing monitored pressure waveform signals in response to the pressure sensed in the conduit;

a processor that receives the monitored pressure waveform signals and determines the flow impedance; and a quality processor that determines the quality of the determined flow impedance.

22. The system of claim 21, wherein the determined flow impedance quality comprises a pressure waveform quality.

23. The system of claim 22, wherein the quality processor reconstructs a pressure waveform from the determined flow impedance, compares the reconstructed pressure waveform to the monitored pressure waveform signals to determine the difference therebetween, and determines the pressure waveform quality as a function of the difference between the reconstructed pressure waveform and monitored pressure waveform signals.

24. The system of claim 23, wherein the quality processor further comprises:

a table for storing estimated flow waveforms corresponding to the selected flow waveform;

a least square estimator that generates coefficients based upon the estimated flow waveforms; and a pressure waveform estimator that receives the coefficients and synthesizes the reconstructed pressure waveform.

25. The system of claim 24, wherein the quality processor further comprises:

an error estimator that compares the reconstructed pressure waveform to the monitored pressure waveform signals on a sample-by-sample basis.

26. The system of claim 24, wherein the flow impedance quality comprises a coefficient quality.

27. The system of claim 26, further comprising:

a parameter quality estimator that determines the quality of the coefficients.

28. The system of claim 27, wherein the parameter quality estimator determines coefficient quality by comparing the coefficients to predetermined ranges.

29. The system of claim 27, further comprising:

a display for presenting indicia of the determined flow impedance quality.

30. The system of claim 21, further comprising:

an alarm that is activated when the determined flow impedance quality is beneath a selected range.

31. A system for monitoring at least one flow parameter in a fluid delivery assembly in which a flow control device acts on a fluid conduit to control the flow of fluid through the conduit, the system comprising:

a pressure sensor coupled to the conduit for providing pressure waveform signals in response to the pressure sensed in the conduit;

a PRBS encoder that outputs a PRBS code; and a processor that receives the PRBS code and controls the flow control device to cause flow in accordance with a pattern of flow variation in accordance with the PRBS code, receives the pressure waveform signals, and processes those pressure waveform signals to determine a flow parameter.

32. The system according to claim 31, wherein the flow parameter comprises the flow impedance.

33. The system according to claim 32 wherein the pseudo-random pattern comprises a pseudo-random binary code.

34. The system according to claim 33 further comprising a selector that selects the rate of fluid flow and outputs a signal corresponding to the selected fluid flow rate to the PRBS encoder.

35. The system according to claim 34, wherein the PRBS encoder generates a PRBS code having a length generally directly proportional to the rate of fluid flow.

36. The system according to claim 34, wherein the PRBS code comprises a predetermined series of ones and zeros corresponding to flow and no flow signals.

37. A method for monitoring a selected flow parameter in a fluid delivery system in which a flow control device acts on a fluid conduit to control the flow of fluid through the conduit, the method comprising the steps of:

(a) controlling the flow control device to cause flow in the conduit in accordance with a pseudo-random pattern of flow variation;

(b) monitoring the pressure in the conduit and providing pressure waveform signals in response to the pressure sensed;

(c) receiving the pressure waveform signals; and (d) processing the pressure waveform signals to determine the selected flow parameter.

38. The method of claim 37, including the further step of:

(e) providing estimated flow waveforms corresponding to the flow caused by the flow control device in the conduit.

39. The method of claim 38, wherein the step of processing the pressure waveform signals comprises processing the pressure waveform signals with the estimated flow waveforms to determine the selected flow parameter.

40. The method of claim 38, including the further step of:

(f) encoding a PRBS code, said pseudo-random pattern of flow variation varying in accordance with the PRBS code.

41. The method of claim 40, including the further step of:

(g) selecting a flow rate;

and wherein step (f) comprises encoding the PRBS code to have a length generally directly proportional to the selected flow rate.

42. A system for monitoring impedance to flow in a fluid delivery assembly in which a flow control device acts on a fluid conduit to control the flow of fluid through the conduit, the system comprising:

a selector for selecting a flow rate;

a comparator that determines if the selected flow rate is a high or a low flow rate by comparing the selected flow rate to a flow rate threshold;

a sensor that monitors pressure in the conduit and provides pressure waveform signals in response to the monitored pressure; and a processor that:

varies the flow rate about the selected flow rate, with the variation in flow rate a function of whether the flow rate is a high or low flow rate;

receives the pressure signal waveform; and calculates the system flow impedance as a function of the pressure waveform signals.

43. The system of claim 42, wherein for high flow rates the processor varies the flow rate at two or more different and discrete flow rates, and wherein the processor determines system flow resistance directly from the changes in flow rate and the pressure waveform signals.

44. The system of claim 42, further comprising:

a table for storing estimated flow waveforms corresponding to the flow of fluid through the conduit.

45. The system of claim 44, wherein for low flow rates the processor:

varies the flow rate in a predetermined pattern about the selected flow rate;

decodes the received pressure waveform signals into decoded pressure signals in accordance with the predetermined pattern; and processes the decoded pressure signals with the estimated flow waveform.

46. A method for determining system flow impedance in a fluid delivery system in which a flow control device acts on a fluid conduit to control the flow of fluid through the conduit, the method comprising the steps of:

(a) selecting a flow rate;

(b) determining if the selected flow rate is a high or low rate by comparing the selected flow rate to a flow rate threshold;

(c) varying the flow ram about the selected flow ram, wherein for high flow rates the flow rate is varied in accordance with a first selected flow rate pattern, and wherein for low flow rates the flow rate is varied in accordance with a second selected flow rate pattern, the second flow rate pattern differing from the first flow rate pattern;

(d) monitoring the pressure in the conduit; and (e) calculating the system flow impedance as a function of the conduit pressure.

47. The method of claim 46, wherein for high flow rates the step of varying the flow rate includes varying the flow rate at two or more different and discrete flow rates, and wherein system resistance is determined directly from the changes in flow rate and conduit pressure.

48. The method of claim 47, wherein the average of the flow rates corresponds to the selected flow rate.

49. The method of claim 46, wherein for low flow rates the step of varying the flow rate includes varying the flow rate in a predetermined pattern about the selected flow rate, and wherein the step of calculating system flow impedance includes the further steps of:

(f) decoding the monitored pressure into decoded pressure signals in accordance with the predetermined pattern; and (g) processing the decoded pressure signals with the flow waveform.

50. The method of claim 49, including the further step of:

(h) determining the resistance from the impedance.

51. The method of claim 50, including the further step of:

(i) displaying the resistance.

52. A method of determining flow impedance in a fluid delivery system in which a flow control device acts on a fluid conduit to control fluid flow through the conduit, the method comprising the steps of:

(a) imparting in the fluid conduit a fluid flow having a selected flow waveform;

(b) monitoring the pressure in the conduit;

(c) providing an estimated flow waveform corresponding to the selected flow waveform; and (d) calculating the flow impedance from the monitored pressure and the estimated flow waveform.

53. The method of claim 52, wherein step (a) comprises the further step of:

(e) controlling the flow control device to cause flow in the conduit in accordance with a pseudo-random pattern of flow variation.

54. The method of claim 53, including the further step of:

(f) encoding a PRBS code, said pseudo-random pattern of flow variation varying in accordance with the PRBS code.

55. The method of claim 52, including the further step of:

(g) determining a quality of the calculated flow impedance.

56. The method of claim 52, wherein the step of calculating the flow impedance comprises the step of:

(h) applying a parameter estimation technique to the monitored pressure and the estimated flow waveform in accordance with a predictive model.

57. The method of claim 56, wherein the step of applying a parameter estimation technique comprises the step of:

(i) applying a least squares estimate fit to the predictive model.

58. The method of claim 57, wherein said predictive model comprises coefficients, said method including the further step of:

(j) determining the flow resistance from the predictive model coefficients.

59. The method of claim 56, wherein the step of applying a parameter estimation technique comprises the step of:

(k) deconvolving the measured pressure signals by the flow waveform.

60. The method of claim 56, wherein the predictive model is a linear predictive model.

61. The method of claim 52, including the further step of:

(l) extracting the fluid resistance from the calculated flow impedance.

62. The method of claim 61, including the further step of:

(m) displaying the resistance.

* * * * *

UNITED STATES PATENT AND TRADEMARK OFFICE
CERTIFICATE OF CORRECTION

PATENT NO. : 5,609,576
DATED : March 11 1997
INVENTOR(S) : Gregory I. Voss, Robert D. Butterfield, Gail D. Baura, Casper W. Barnes It is certified that error appears in the above-indentified patent and that said Letters Patent is hereby corrected as shown below:

Column 13, Claim 12, Line 20, after "a processor that;" delete "should be:".

Column 17, Claim 46, Line 27, change "ram" -two occurences, to read --rate--.

Signed and Sealed this

Twenty-first Day of October 1997

BRUCE LEHMAN

Attest:

Attesting Officer

Commissioner of Patents and Trademarks